US000001893H

United States Statutory Invention Registration [19]

[11] Reg. Number: H1,893

Patel et al. [45] Published: Oct. 3, 2000

[54] ENZYMATIC REDUCTION METHOD FOR THE PREPARATION OF HALOHYDRINS

[75] Inventors: Ramesh N. Patel, Bridgewater; Laszlo J. Szarka, East Brunswick, both of N.J.; Amit Banerjee, Yardley, Pa.; Clyde G. McNamee, Lawrenceville, N.J.

[73] Assignee: Bristol-Myers Squibb Company, Princeton, N.J.

[21] Appl. No.: 08/685,318

[22] Filed: Jul. 23, 1996

[51] Int. Cl.[7] ..... C12P 13/02; C07C 1/04; C12N 1/00

[52] U.S. Cl. ..... 435/129; 435/280; 435/822

[58] Field of Search ..... 435/280, 106–110, 435/113–116

[56] References Cited

U.S. PATENT DOCUMENTS 5,481,011 1/1996 Chen et al. ..... 549/514

OTHER PUBLICATIONS

Christen M. et al., Biotransformation in Organic Synthesis: Applications of Yeast Reduction in the Synthesis of 3,5–Dihydroxy Esters of High Optical Plurity, J. Chem. Soc. Chem. Comm. 1988: 264–266.

*Primary Examiner*—Charles T. Jordan
*Assistant Examiner*—Aileen J. Baker
*Attorney, Agent, or Firm*—Suzanne E. Babajko

[57] ABSTRACT

An enzymatic reduction method, particularly a stereoselective enzymatic reduction method, for the preparation of halohydrins from haloketones. The halohydrin products are particularly useful in the preparation of epoxides, which may be employed as intermediates in the preparation of protease inhibitors such as retroviral protease inhibitors.

1 Claim, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ENZYMATIC REDUCTION METHOD FOR THE PREPARATION OF HALOHYDRINS

FIELD OF THE INVENTION

The present invention relates to an enzymatic reduction method for the conversion of haloketones to halohydrins, and particularly to stereoselective such methods. The halohydrins prepared are useful, for example, as intermediates in the preparation of protease inhibitors.

BACKGROUND OF THE INVENTION

Proteases are enzymes which cleave proteins at specific peptide bonds and, in living systems, mediate or control a broad spectrum of biological functions, such as cleaving precursors to form active proteins in post-translational processing of polypeptides. Inhibiting proteases vital to certain biological functions thus provides a means for the treatment or prevention of disease states which rely on the action of the proteases involved.

For example, retroviral proteases, such as HIV protease, cleave large precursor polypeptides, produced in infected cells, into smaller protein components, or subunits, which are subsequently assembled to form functional virus structures. Since such proteases encoded by the viral genome play a critical role in the replication of a virus, inhibition of these enzymes provides a means for the prevention and treatment of retroviral infection. Various retroviral proteases have been disclosed for this purpose; see, for example, European Patent Application 346,847, and especially European Patent Application 580,402.

As another example, renin is a protease which cleaves angiotensinogen to form angiotensin I, the latter which is then cleaved by a second enzyme (ACE) to form angiotensin II, a potent hypertensive agent. Inhibition of renin provides a means for controlling hypertension, and inhibitors may be prepared for this purpose. See, for example, Luly et al., *J. Org. Chem.,* 52, 1487–1492 (1987) and Evans et al., *J. Org. Chem.,* 50, 4615–4625 (1985).

Depending on their structure, protease inhibitors, such as those described above, may be prepared using epoxide intermediates. As such epoxides may be prepared from halohydrins, methods for the preparation of the halohydrin starting materials are sought. Additionally, as with many pharmaceutical agents, the stereoconfiguration of protease inhibitors can play a role in their effectiveness. Since a protease inhibitor having a desired stereoconfiguration is often most efficiently prepared by employing the appropriate chiral precursors, stereoselective methods for the preparation of the epoxide intermediates and the halohydrin starting materials are particularly sought.

SUMMARY OF THE INVENTION

The present invention provides a method for the enzymatic reduction, preferably, the stereoselective enzymatic reduction, of haloketone, in particular halomethyl ketone, compounds to form halohydrin compounds, particularly useful as intermediates in the preparation of epoxides.

Specifically, the present invention provides a method for the enzymatic reduction of a compound of the formula I or a salt thereof:

(I)

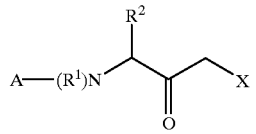

to form a compound of the formula II or a salt thereof:

(II)

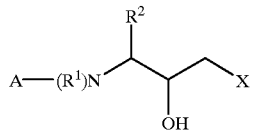

where

A is:

(1) hydrogen;

(2) alkyl;

(3) $R^3-\underset{\underset{Z}{\|}}{C}-$ ;

(4) $R^3-SO_2-$ ;

(5) $R^3-\underset{\underset{R^4}{|}}{N}-SO_2-$ ;

(6) $R^3-\underset{\underset{R^4}{|}}{N}-\underset{\underset{Z}{\|}}{C}-$ ;

(7) $R^3-S-\overset{\overset{O}{\|}}{C}-$ ;

(8) $R^5-\underset{\underset{R^7}{|}}{\overset{\overset{R^6}{|}}{C}}-O-\overset{\overset{Z}{\|}}{C}-$ ; or (9) $R^3-SO-$ ;

$R^1$ is:

(1) hydrogen; or (2) alkyl;

$R^2$ is alkyl, preferably (1) unsubstituted lower alkyl; or (2) substituted lower alkyl, most preferably:

(A) cycloalkylalkyl;

(B) heterocycloalkyl;

(C) arylalkenylalkyl; or (D) arylalkyl;

where, in (A), (B), (C), and (D), alkyl is lower alkyl;

$R^3$ and $R^4$ are independently:

(1) hydrogen;

(2) alkyl;

(3) aryl;

(4) heterocyclo;

(5) carbocyclo; or (6) when $R^3$ and $R^4$ are bonded to a common nitrogen atom, $R^3$ and $R^4$ may be joined, together with that nitrogen atom, to form a heterocyclic ring system; and $R^5$, $R^6$ and $R^7$ are independently:

(1) hydrogen;

(2) alkyl;

(3) aryl;

(4) carbocyclo;

(5) fluorenyl;

(6) heterocyclo;

(7) $R^5$, $R^6$ and $R^7$ may, independently, be joined, together with the carbon atom to which they are bonded, to form a mono-, bi- or tricyclic carbocyclic ring system, or a mono-, bi- or tricyclic heterocyclic ring system;

(8) alkynyl; or (9) alkenyl;

Z is oxygen or sulfur; and

X is a halogen, such as chlorine, bromine or iodine;

comprising the step of contacting said compound of the formula I or salt thereof with an oxidoreductase enzyme, or oxidoreductase enzyme-supplying microorganism, capable of catalyzing the reduction of said compound of the formula I or salt thereof to form said compound of the formula II or salt thereof, and effecting said reduction.

The group X of the above compounds is a leaving group capable of forming, with the hydroxyl group of the compound of the formula II or salt thereof, an epoxide ring.

The carbon atom bearing the group $R^2$ and adjacent to the carbonyl group in the compound of the formula I is chiral, so that the starting compound of the formula I or salt thereof may have either of the following configurations Ia or Ib:

(Ia)

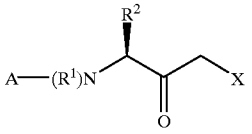

(Ib)

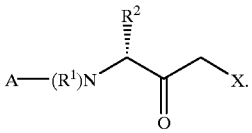

Compounds of the formula Ia have the same absolute stereoconfiguration at the carbon atom bearing the $R^2$ group as the compound (1S)-[3-chloro-2-oxo-1-(phenylmethyl) propyl]carbamic acid, 1,1-dimethylethyl ester. Compounds of the formula Ib have the same absolute stereoconfiguration at the corresponding carbon atom as the compound (1R)[3-chloro-2-oxo-1-(phenylmethyl)propyl]carbamic acid, 1,1-dimethylethyl ester.

With respect to the aforementioned chiral carbon atom, the starting compound of the formula I or salt thereof may be employed as a single isomer (Ia or Ib) or as a mixture of both Ia and Ib isomers (for example, as a racemate). Preferably, however, the starting compound of the formula I or salt thereof is employed in the Ia stereoconfiguration, substantially free of the compound in the Ib stereoconfiguration.

When a compound of the formula Ib or salt thereof substantially free of the compound of the formula Ia or salt thereof is reduced, the following stereoisomers IIc and/or IId of the formula II may be formed:

(IIc)

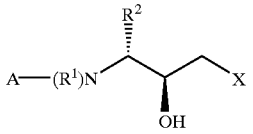

(IId)

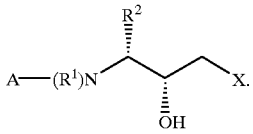

When a compound of the formula Ia or salt thereof substantially free of the compound of the formula Ib or salt thereof is reduced, the following stereoisomers IIa and/or IIb of the formula II may be formed:

(IIa)

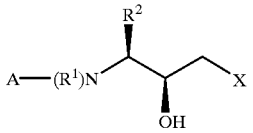

(IIb)

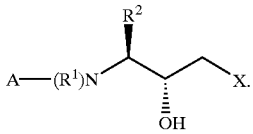

A particularly preferred embodiment of the present invention provides a method for the stereoselective enzymatic reduction of a compound of the formula Ia or salt thereof to form a compound of the formula IIa or salt thereof, comprising the step of contacting said compound of the formula Ia or salt thereof with an oxidoreductase enzyme, or oxidoreductase enzyme-supplying microorganism, capable of catalyzing said stereoselective reduction, and effecting said reduction. Compounds of the formula IIa have the same absolute stereoconfiguration at the carbon atom bearing the hydroxyl group as the compound (1S, 2R)-[3-chloro-2-hydroxy-1-(phenylmethyl)propyl]carbamic acid, 1,1-dimethylethyl ester. Compounds of the formula IIb have the same absolute stereoconfiguration at the corresponding carbon atom as the compound (1S,2S)-[3-chloro-2-hydroxy-1-(phenylmethyl)propyl]carbamic acid, 1,1-dimethylethyl ester. As described above, the starting compound of the formula Ia or salt thereof is preferably substantially free of compound Ib or salt thereof.

DETAILED DESCRIPTION OF THE INVENTION

The methods of the present invention are described further as follows.

Definitions

The terms "alk" or "alkyl", as employed herein alone or as part of another group, denote both straight and branched chain, optionally substituted saturated radicals, for example, containing 1 to 12 carbons, most preferably 1 to 8 carbons, in the normal chain. It is understood, therefore, that throughout this specification the terms "alk" and "alkyl" denote both unsubstituted groups such as methyl, ethyl, n-propyl, isopropyl, n-butyl, iso-butyl, sec-butyl, tert-butyl, n-pentyl, 1-methylbutyl, 2,2-dimethylbutyl, 2-methylpentyl, n-hexyl and the like, as well as substituted groups such as phenylmethyl and the like. Exemplary substituents may include one or more, such as 1, 2 or 3, of the following:

(1) hydroxy (or protected hydroxy);

(2) oxo (i.e. =O), with the proviso that the carbon bearing the oxo group is not adjacent to a heteroatom;

(3) carboxy;

(4) halo (especially to form trihaloalkyl, particularly trifluoromethyl);

(5) alkoxy, such as phenyl-lower alkoxy or $$R^{16}—[O—(CH_2)_m]_n—O—$$

where m is an integer from 2 to 5; n is an integer from 1 to 5; and $R^{16}$ is:

(a) hydrogen;

(b) alkyl, especially unsubstituted lower alkyl or alkoxy-lower alkyl;

(c) aryl; or (d) heterocyclo;

(6) aryloxy;

(7) alkoxycarbonyl;

(8)

$$(R^{12})(R^{13})N—\underset{\underset{O}{\|}}{C}— \;;$$

where $R^{12}$ and $R^{13}$ are independently:

(a) hydrogen;

(b) alkyl, especially lower alkyl;

(c) aryl;

(d) heterocyclo;

(e) carbocyclo, such as cycloalkyl;

(f) $R^{12}$ and $R^{13}$ may be joined, together with the nitrogen atom to which they are bonded, to form a 5 to 7 membered heterocyclic ring;

(9) $(R^{12})$ $(R^{13})N—$, such as amino (H2N—);

(10)

$$R^{15}—\overset{\overset{O}{\|}}{C}—\underset{\underset{R^{16}}{|}}{N}—$$

where $R^{14}$ is:

(a) hydrogen;

(b) alkyl, especially lower alkyl;

(c) aryl;

(d) heterocyclo;

(e) carbocyclo, such as cycloalkyl; or (f) $R^{14}$ and $R^{15}$ may be joined to form an alkylene group of three to five carbon atoms; and $R^{15}$ is:

(a) hydrogen;

(b) alkyl, especially lower alkyl;

(c) alkenyl, especially lower alkenyl;

(d) aryl;

(e) heterocyclo;

(f) carbocyclo, such as cycloalkyl;

(g)

$$R^5—\overset{\overset{R^6}{|}}{\underset{\underset{R^7}{|}}{C}}—O— \;,$$

wherein $R^5$, $R^6$ and $R^7$ are, independently, those groups (1) through (9) recited for $R^5$, $R^6$ and $R^7$ above; or (h) $R^{15}$ may be joined together with $R^{14}$ as described above;

(11)

$$R^{15}—SO_2—\underset{\underset{R^{14}}{|}}{N}— \;;$$

(12) carbocyclo, such as cycloalkyl;

(13) heterocyclo;

(14) heterocyclooxy;

(15) aryl, such as phenyl;

(16) alkylcarbonyloxy, such as lower alkylcarbonyloxy;

(17) arylcarbonyloxy;

(18) cyano;

(19) mercapto;

(20) alkenyl;

(21) alkynyl, such as ethynyl (e.g., forming a propargyl group);

(22) alkylthio;

(23) arylthio;

(24) trialkylsilyl, such as trimethylsilyl;

(25) azo (i.e., $R^{16}O—N=$ where $R^{16}$ is as defined above, preferably hydrogen (to form an oxime group (HO—N=)) or unsubstituted alkyl (to form an unsubstituted alkoxyimino group (alkyl—O—N=)); or

(26) $(R^{12})$ $(R^{13})N—C(O)—O—$, where $R^{12}$ and $R^{13}$ are as defined above.

The term "alkoxy" denotes an alkyl group bonded through an oxygen bridge (—O—); the term "alkylthio" denotes an alkyl group bonded through a sulfur bridge (—S—); the term "alkoxycarbonyl" (also referred to as "carboalkoxy") denotes an alkoxy group attached to a carbonyl group to form an ester; the term "alkylcarbonyloxy" denotes an alkyl group bonded to a carbonyl group which is in turn bonded through an oxygen bridge; the term "aminocarbonyloxy" denotes an amino group bonded through a carbonyl group which is, in turn, bonded through an oxygen bridge; the term "alkylaminocarbonyloxy" denotes an alkyl group bonded through an aminocarbonyloxy group as described above; the term "alkylaminocarbonyl" denotes an alkyl group bonded through an amino group which is, in turn, bonded through a carbonyl group; and the term "alkylene" denotes a divalent alkyl group. With respect to exemplary alkyl groups which are substituted, the term "alkoxy-alkyl" specifically denotes an alkoxy group bonded through an alkyl group; the term "aryl-alkyl" specifically denotes an aryl group bonded through an alkyl group; the term "heterocyclo-alkyl" specifically denotes a heterocyclo group bonded through an alkyl group; the term "cycloalkyl-alkyl" specifically denotes a cycloalkyl group bonded through an alkyl group; and the term "hydroxy-alkyl" specifically denotes one or more hydroxyl groups attached to an alkyl group. In each of the aforementioned terms, "alkyl" may be further substituted, or unsubstituted, as defined above. Similarly, the terms "arylalkoxy", "alkoxyalkoxy", "hydroxyalkoxy", "heterocycloalkoxy", "aminoalkoxyl", "aminocarbonyloxyalkoxy", "heterocyclocarbonylalkoxy", "heterocyclooxyalkoxy", "alkoxycarbonylalkoxy" and "carboxyalkoxy" specifically denote alkoxy substituted by aryl, alkoxy, hydroxy, heterocyclo, amino, aminocarbonyloxy, heterocyclocarbonyl, heterocyclooxy, alkoxycarbonyl and carboxy, respectively.

The term "lower alkyl", as employed herein alone or as part of another group, denotes optionally substituted groups as described above for alkyl containing 1 to 6 carbon atoms in the normal chain. Lower alkyl groups are preferred alkyl groups.

The term "alkenyl", as employed herein alone or as part of another group, denotes both straight and branched chain, optionally substituted radicals, for example, containing 2 to 12 carbons in the normal chain, most preferably 2 to 8 carbons, which contain at least one carbon to carbon double bond and which are directly attached through one of the carbons composing the double bond. It is understood, therefore, that throughout his specification, the term "alkenyl" denotes both unsubstituted groups such as ethenyl, propenyl, butenyl, pentenyl, hexenyl, and the like, as well as substituted groups. Exemplary substituents may include one or more, such as 1, 2 or 3, of the following:

(1) alkyl, especially lower alkyl;

(2) aryl;

(3) carbocyclo, such as cycloalkyl;

(4) heterocyclo;

(5) carboxy;

(6) halo;

(7)

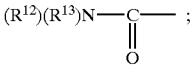

(8) cyano;

(9) alkoxycarbonyl;

(10) trialkylsilyl; or

(11) alkynyl.

The term "lower alkenyl", as employed herein alone or as part of another group, denotes optionally substituted groups as described above for alkenyl containing 2 to 6 carbon atoms in the normal chain. Lower alkenyl groups are preferred alkenyl groups.

The term "alkynyl", as employed herein alone or as part of another group, denotes both straight and branched chain, optionally substituted radicals, for example, containing 2 to 12 carbons in the normal chain, most preferably 2 to 8 carbons, which contain at least one carbon to carbon triple bond and which are directly attached through one of the carbons composing the triple bond. It is understood, therefore, that throughout this specification, the term "alkynyl" denotes both unsubstituted groups such as ethynyl, methyl-ethynyl, and the like, as well as substituted groups. Exemplary substituents may include one or more, such as 1, 2 or 3, of the following:

(1) alkyl, especially lower alkyl;

(2) aryl;

(3) carbocyclo, such as cycloalkyl;

(4) heterocyclo;

(5) carboxy;

(6)

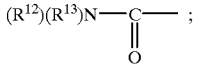

(7) cyano;

(8) alkoxycarbonyl;

(9) alkenyl; or

(10) trialkylsilyl.

The terms "carbocyclo", "carbocyclic" or "carbocyclic ring system", as employed herein alone or as part of another group, denote an optionally substituted, saturated or partially unsaturated, homocyclic carbon ring system, such as a cycloalkenyl ring system, which is partially unsaturated, or most preferably, a cycloalkyl ring system, which is fully saturated, wherein the aforementioned cycloalkenyl and cycloalkyl ring systems are, according to the above definition, optionally substituted. Such cyclic groups preferably contain from 1 to 3 rings and from 3 to 12, most preferably from 3 to 7, carbons per homocyclic ring. It is understood, therefore, that throughout this specification the terms "carbocyclo", "carbocyclic" and "carbocyclic ring system" denote both unsubstituted groups exemplified by monocyclic groups such as cyclopropyl, cyclobutyl, cyclopentyl, cyclohexyl and cycloheptyl; bicyclic groups such as octahydropentalenyl, decalin, norbornyl, spirocycloheptyl (e.g. spiro[2.4]heptyl), spirocyclooctyl (e.g. spiro[3.4]octyl), spirocyclononyl (e.g. spiro[4.4]nonyl), and the like; and tricyclic groups such as adamantyl, as well as substituted groups. Exemplary substituents may include one or more, such as 1, 2 or 3, of the following:

(1) alkyl, especially lower alkyl;

(2) hydroxy (or protected hydroxy);

(3) halo;

(4) mercapto;

(5) cyano;

(6) carboxy;

(7) alkoxycarbonyl;

(8)

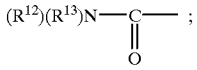

(9) alkylcarbonyloxy, such as lower alkylcarbonyloxy;

(10) arylcarbonyloxy;

(11) $(R^{12})(R^{13})N$—, such as amino ($H_2N$—);

(12) alkoxy;

(13) aryl, such as where said aryl group is bonded through a single bond or is fused to said carbocyclo group (e.g. to form a tetrahydronaphthyl, indanyl or indenyl group), and wherein, in each case, the aryl-carbocyclo moiety so formed is bonded through the carbocyclo group;

(14) heterocyclo;

(15) heterocyclooxy;

(16) oxo (=O);

(17) aryloxy;

(18) alkylthio;

(19) arylthio;

(20)

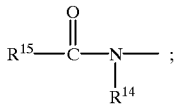

(21) alkenyl;

(22) alkynyl; or

(23) trialkylsilyl.

The terms "ar" or "aryl", as employed herein alone or as part of another group, denote homocyclic, optionally substituted aromatic groups, preferably monocyclic or bicyclic groups containing from 6 to 12 carbons in the ring portion, such as phenyl, naphthyl, tetrahydronaphthyl, indanyl, biphenyl and the like. It is understood, therefore, that throughout this specification, the terms "ar" and "aryl" denote unsubstituted as well as substituted groups. Exemplary substituents may include one or more, such as 1, 2 or 3, of the following:

(1) alkyl, especially lower alkyl;

(2) alkoxy;

(3) hydroxy (or protected hydroxy);

(4) halo;

(5) $(R^{12})$ $(^{13})N$—, such as amino $(H_2N—)$ (6) alkylthio;

(7) mercapto;

(8) nitro;

(9) cyano;

(10) carboxy;

(11) carboalkoxy;

(12) carbocyclo, such as where said carbocyclo group is bonded through a single bond, or is fused to said aryl group (e.g. to form a tetrahydronaphthyl, indanyl or indenyl group), and wherein, in each case, the carbocyclo-aryl moiety so formed is bonded through the aryl group;

(13)

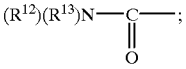

(14) $(R^{12})(R^{13})N—SO_2—$;

(15)

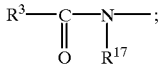

where $R^{17}$ is:

(a) hydrogen;

(b) alkyl, especially lower alkyl;

(c) aryl;

(d) heterocyclo;

(e) carbocyclo, such as cycloalkyl; or (f) $R^{17}$ may, together with $R^3$, form an alkylene group of three to five carbons;

(16)

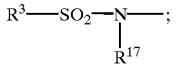

(17) phenyl;

(18) alkylcarbonyloxy, such as lower alkylcarbonyloxy;

(19) arylcarbonyloxy;

(20) arylthio;

(21) heterocyclooxy;

(22) aryloxy;

(23) alkylthio; or

(24) alkenyl.

The term "arylcarbonyloxy" denotes an aryl group which is bonded through a carbonyl group which is, in turn, bonded through an oxygen bridge; the term "aryloxy" denotes on aryl group bonded through an oxygen bridge; the term "arylcarbonyl" denotes an aryl group bonded through a carbonyl group; the term "arylaminocarbonyl" denotes an aryl group bonded through an amino group which is, in turn, bonded through a carbonyl group; and the term "arylthio" denotes an aryl group bonded through a sulfur bridge.

The terms "halogen" or "halo", as employed herein alone or as part of another group, refer to chlorine, bromine, fluorine and iodine.

The terms "heterocyclo", "heterocyclic" or "heterocyclic ring system", as employed herein alone or as part of another group, denote an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclo group containing a heteroatom may have 1, 2 or 3 heteroatoms selected from nitrogen atoms, oxygen atoms or sulfur atoms, where the nitrogen and sulfur heteroatoms may optionally be oxidized and the nitrogen heteroatoms may optionally be quaternized. The heterocyclo group may be attached at any heteroatom or carbon atom.

Exemplary monocyclic heterocyclo groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazoyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like.

Exemplary bicyclic heterocyclo groups include indolyl, benzothiazolyl, benzoxazolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, dihydroindazolyl such as the group:

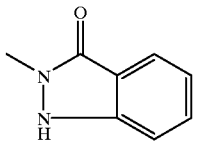

furopyridinyl (such as furo[2,3-c]pyridinyl, furo[3,2-b]pyridinyl, or furo[2,3-b]pyridinyl), dihydroisoindolyl, dihydroquinazolinyl (such as 3,4-dihydro-4-oxo-quinazolinyl), and the like.

Exemplary tricyclic heterocyclo groups include carbazolyl, benzindolyl, phenanthrolinyl, acridinyl, phenanthridinyl, xanthenyl, and the like.

It is understood that throughout this specification the terms "heterocyclo", "heterocyclic" and "heterocyclic ring system" denote both unsubstituted as well as substituted groups. Exemplary heterocyclo substituents may include one or more, such as 1, 2 or 3, of the following:

(1) alkyl, especially lower alkyl;

(2) hydroxy (or protected hydroxy);

(3) halo;

(4) oxo (i.e. =O);

(5) $(R^{12})(R^{13})N$—, such as amino ($H_2N$—);

(6) alkoxy;

(7) carbocyclo, such as cycloalkyl;

(8) carboxy;

(9) heterocyclooxy;

(10) alkoxycarbonyl, such as unsubstituted lower alkoxycarbonyl;

(11)

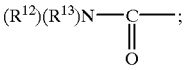

(12) mercapto;

(13) nitro;

(14) cyano;

(15) carboalkoxy;

(16) $(R^{12})(R^{13})N—SO_2$—;

(17)

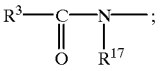

(18)

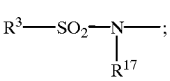

(19) aryl;

(20) alkylcarbonyloxy;

(21) arylcarbonyloxy;

(22) arylthio;

(23) aryloxy;

(24) alkylthio; or

(25) formyl.

The term "heterocyclooxy" denotes a heterocyclo group bonded through an oxygen bridge; and the term "heterocyclocarbonyl" denotes a heterocyclo group bonded through a carbonyl group.

The term "hydroxyl protecting group", as used herein, denotes any group known as or capable of functioning as a hydroxyl protecting group, such as those groups so described in "Protective Groups in Organic Synthesis" by T. W. Greene, John Wiley and Sons, 1991, or Fieser & Fieser. Exemplary hydroxyl protecting groups include benzyl, trialkylsilyl, acetate and benzoate.

The term "carboxy", as used herein alone or as part of another group, denotes the carboxylic acid group —COOH.

The term "amino acid", as used herein alone or as part of another group, preferably denotes the group:

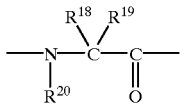

where $R^{18}$ and $R^{19}$ are independently:

(1) hydrogen;

(2) alkyl, especially lower alkyl;

(3) alkenyl, especially lower alkenyl;

(4) aryl;

(5) heterocyclo;

(6) carbocyclo, such as cycloalkyl;

(7) $R^{18}$ and $R^{19}$ may be joined, together with the carbon atom to which they are bonded, to form a carbocyclo group, such as a 4- to 7-membered cycloalkyl ring; or (8) $R^{18}$ and $R^{20}$ may be joined as described in the definition of $R^{20}$ following;

$R^{20}$ is:

(1) hydrogen;

(2) alkyl, especially lower alkyl;

(3) aryl;

(4) heterocyclo;

(5) carbocyclo, such as cycloalkyl; or (6) $R^{18}$ and $R^{20}$ may be joined, together with the atoms to which they are bonded, to form a heterocyclic group, such as a 4 to 7 membered, saturated monocyclic heterocyclic ring which may be unsubstituted or substituted by groups such as:

(i) hydrogen;

(ii) alkyl, especially lower alkyl;

(iii) alkenyl, especially lower alkenyl;

(iv) aryl, for example, where said aryl group is bonded through a single bond, or is fused to said monocyclic heterocyclic ring to form an unsaturated bicyclic heterocyclic ring system;

(v) heterocyclo;

(vi) mercapto;

(vii) alkoxy;

(viii) carbocyclo, such as cycloalkyl, for example, where said cycloalkyl group is bonded through a single bond, or is fused or spirofused to said monocyclic heterocyclic ring to form a saturated bicyclic heterocyclic ring system;

(ix) hydroxyl (or protected hydroxyl);

(x) aryloxy;

(xi) alkylthio;

(xii) arylthio; or (xiii) oxo.

The amino acid moiety described above includes, for example, such moieties as may be found in D and L alanine, asparagine, aspartic acid, arginine, cysteine, glycine, glutamine, glutamic acid, histidine, isoleucine, leucine, lysine, methionine, phenylalanine, serine, homoserine, threonine, tryptophan, tyrosine, valine, hydroxyvaline, norleucine, norvaline, phenylglycine, cyclohexylalanine, t-butylglycine (t-leucine), hydroxy-t-butylglycine, amino butyric acid, ornithine, and cycloleucine, and preferably, when $R^{18}$ and $R^{20}$ are joined, together with the atoms to which they are bonded, proline, 4-hydroxyproline, pyroglutamic acid, azetidine carboxylic acid, pipecolinic acid, indoline-2-carboxylic acid, tetrahydro-3-isoquinoline carboxylic acid,

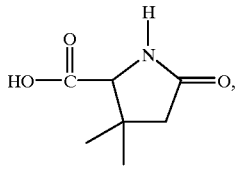

and

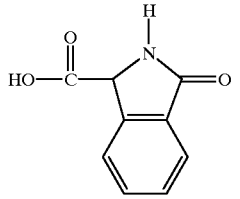

The term "peptide chain", as used herein, denotes two or more amino acids as described above bonded through a peptide linkage

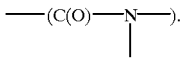

The "N-terminus" of the above-described amino acid(s) denotes the —N($R^{20}$)— group.

The term "salt(s)", as employed herein, denotes acidic and/or basic salts formed with inorganic and/or organic acids and bases. Zwitterions (internal or inner salts) are included within the term "salt(s)" as used herein, as are quaternary ammonium salts such as alkylammonium salts. The nontoxic, pharmaceutically acceptable salts are preferred, although other salts may be useful, for example, in isolation or purification steps which may be employed during preparation.

Exemplary acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, thiocyanate, tosylate, and undecanoate.

Exemplary basic salts include ammonium salts, alkali metal salts such as sodium, lithium, and potassium salts, alkaline earth metal salts such as calcium and magnesium salts, salts with organic bases such as dicyclohexylamine, N-methyl-D-glucamine, and salts with amino acids such as arginine, lysine and so forth. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

The terms "stereoselective enzymatic reduction" and "stereoselective reduction", as used herein, refer, with respect to the carbon atom bearing the hydroxyl group formed by the reduction, to the preferential formation of one enantiomer of a compound of the formula II (that is, formation of that enantiomer in greater quantity, and preferably, exclusively) relative to the formation of the other enantiomer thereof. For example, in a preferred embodiment of the present invention, stereoselective reduction of a compound of the formula Ia provides preferential formation of a compound of the formula IIa relative to a compound of the formula IIb.

The term "mixture", as said term is used herein in relation to stereoisomeric, such as enantiomeric compounds, includes mixtures having equal (i.e., racemic for an enantiomeric mixture) or non-equal amounts of stereoisomers.

The terms "enzymatic process" or "enzymatic method", as used herein, denote a process or method of the present invention employing an enzyme or microorganism.

The term "substantially free", as used herein with respect to one compound relative to one or more other compounds, denotes that the former is pure or contains only trace amounts of the latter.

The term "oxidoreductase enzyme-supplying microorganism", as used herein, denotes a microorganism which contains or produces, intracellularly and/or extracellularly, one or more oxidoreductase enzyme(s).

Salts or solvates such as hydrates of reactants or products may be employed or prepared as appropriate in any of the methods of the present invention. Tautomers of reactants or products are contemplated where appropriate.

The initial definition provided for a group or term herein applies to that group or term throughout the present specification, unless otherwise indicated. It is to be understood that "exemplary" groups recited herein are illustrative and not limiting. Throughout this specification, groups and substituents thereof may be chosen to provide stable moieties and compounds.

All stereoisomers of reactants and products are contemplated within the scope of this invention, unless otherwise indicated. Individual stereoisomers of such compounds may, for example, be substantially free of other isomers, or may be admixed, for example, as racemates or with all other, or other selected, stereoisomers. The chiral centers of the present invention can have the S or R configuration as defined by the IUPAC 1974 Recommendations.

Starting Materials

The starting haloketones of the formula I and salts thereof employed in the present reduction method may be obtained by any suitable means, such as by the conversion, by known methods, of a nitrogen protected amino acid (e.g., BOC—NH—CH($R^2$)—COOH) or a carboxylic acid protected amino acid (e.g., HCl•$NH_2$—CH($R^2$)—COO(protecting group)) to a compound of the formula I or salt thereof. The starting haloketones may, for example, be prepared by methods described in, or by methods analogous to those described in, European Patent Application No. 580,402, or U.S. application Ser. No. 08/355,373, filed Dec. 13, 1994 by Chen et al. entitled "Process for Preparing N-Protected Amino Acid a-Halomethyl Ketones and Alcohols From N-Protected Amino Acid Esters."

Preferred Compounds

Compounds having the following groups are referably employed in or prepared by the methods f the present invention.

A is preferably a group selected from those groups (3) to (9) defined above, particularly:

the group (3):

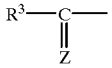

where

Z is sulfur or, most preferably, oxygen;

$R^3$ is preferably hydrogen; aryl (e.g., phenyl or naphthyl); alkyl which is unsubstituted (e.g., methyl, ethyl or tert-butyl) or substituted by one or more of oxo, hydroxy (e.g., mono- or dihydroxy) or protected hydroxy, aryloxy (e.g., phenoxy or naphthyloxy), alkoxy (e.g., methoxy, benzyloxy, or benzimidazolylpropoxy), aryl (e.g., phenyl), heterocyclo (e.g., benzimidazolyl, 1,3-dioxolane (optionally substituted by methyl groups), indolyl, pyridyl, or dihydroindazolyl (optionally substituted by oxo)), oxime, alkoxyimino (e.g., methoxyimino), amino or substituted amino (e.g., benzyloxycarbonylamino), alkylaminocarbonyl (e.g., N-methylaminocarbonyl), arylaminocarbonyl (e.g., phenylaminocarbonyl), alkylaminocarbonyloxy (e.g., N-methylaminocarbonyloxy), or fluoro (e.g., to form trifluoromethyl); carbocyclo (e.g., cyclopentyl or cyclohexyl (optionally substituted by methyl and/or hydroxy groups), or indanyl (optionally further substituted by hydroxy); or heterocyclo (e.g., quinolinyl, pyrrolidinyl (optionally substituted by methyl and/or oxo groups), oxazolidinyl (optionally substituted by methyl and/or oxo groups), dihydroisoindolyl (optionally substituted by formyl, tetrahydrofuryl (optionally substituted by hydroxy and/or methyl groups), or benzimidazolyl); $R^3$ is most preferably carbocyclo or alkyl wherein the carbocyclo or alkyl groups are substituted, particularly by one or more of hydroxy, aryl, heterocyclo, alkylaminocarbonyl or fluoro (especially to form trifluoromethyl);

the group (4):

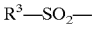

where $R^3$ is alkyl, especially unsubstituted lower alkyl;

the group (6):

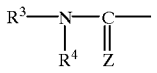

where Z is sulfur or, most preferably, oxygen;

$R^3$ preferably alkyl such as unsubstituted lower alkyl (e.g., methyl or tert-butyl), arylalkyl (e.g., benzyl), or heterocycloalkyl (e.g., pyridylmethyl or benzimidazolylmethyl); and $R^4$ is preferably alkyl such as unsubstituted lower alkyl (e.g., methyl) or, most preferably, $R^4$ is hydrogen;

the group (8):

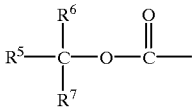

where $R^5$ is preferably hydrogen; carbocyclo (e.g., indenyl); alkyl such as unsubstituted lower alkyl (e.g., methyl, ethyl or tert-butyl) or alkyl which is substituted by one or more of amino, substituted amino (e.g., amino substituted by formyl, phenyl, benzyl or benzyloxycarbonyl), halo (e.g., fluoro), aryl (e.g., phenyl), hydroxy (e.g., mono or dihydroxy) or protected hydroxy, heterocyclo (e.g., dihydroindazolyl (optionally substituted by oxo and/or benzyl)), alkoxy (such as unsubstituted lower alkoxy (e.g., methoxy) or arylalkoxy (e.g., benzyloxy)), aryloxy (e.g., phenoxy), or arylaminocarbonyl (e.g., phenylaminocarbonyl); aryl (e.g., phenyl or biphenyl); heterocyclo (e.g., imidazolyl (optionally substituted by trityl and/or phenyl), oxazolyl (optionally substituted by phenyl), 2-furo[2,3-c]pyridinyl, 2-furo[3,2-b]pyridinyl, 2-furo[2,3-b]pyridinyl, quinoxalinyl, benzothiazolyl, quinolinyl, benzimidazolyl (optionally substituted by benzyloxymethyl), pyridyl, indolyl, oxazolidinyl (optionally substituted by oxo), dihydroisoindolyl (optionally substituted by oxo), 1,3-dioxolane (optionally substituted by methyl groups), dihydroquinazolinyl (optionally substituted by oxo), or benzoxazolyl); fluoren-9-yl; or alkynyl (e.g., phenylalkynyl); $R^5$ is most preferably hydrogen, alkyl (unsubstituted or substituted, in the latter case preferably hydroxyalkyl), aryl or heterocyclo;

$R^6$ and $R^7$ are preferably hydrogen, or alkyl such as unsubstituted lower alkyl (e.g., methyl) or hydroxyalkyl; or two of $R^5$, $R^6$ and $R^7$, together with the carbon atom to which they are bonded, form a carbocyclo group (e.g., cyclobutyl or cyclopentyl (optionally substituted by hydroxy), or indanyl (optionally further substituted by hydroxy or protected hydroxy)), or a heterocyclo group (e.g., oxetanyl, tetrahydrofuryl (optionally substituted by hydroxy), tetrahydro-1,1-dioxothienyl, tetrahydropyranyl, or benzimidazolyl (optionally substituted by methyl)); or the group (9):

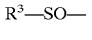

where $R^3$ is alkyl, especially unsubstituted lower alkyl.

$R^1$ is preferably hydrogen or unsubstituted lower alkyl (e.g., methyl), most preferably hydrogen.

$R^2$ is preferably unsubstituted lower alkyl (e.g., sec-butyl or isobutyl); or substituted lower alkyl, most preferably:

(A) cycloalkylalkyl (e.g., cyclohexylmethyl);

(B) heterocycloalkyl, especially heterocyclomethyl (e.g., indolylmethyl, pyridylmethyl, or quinolinylmethyl);

(C) arylalkenylalkyl, particularly where aryl is substituted by a group Ar(sub) defined below; or (D) arylalkyl, for example, phenylethyl, or, especially, a group of the formula:

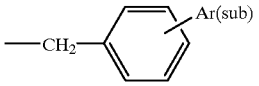

where Ar(sub) is:

(i) hydrogen;

(ii) hydroxy;

(iii) alkenyl (e.g., ethenyl);

(iv) alkyl, especially unsubstituted lower alkyl (e.g., ethyl); or (v) alkoxy, especially:

unsubstituted lower alkoxy (e.g., methoxy);

alkoxyalkoxy (e.g., methoxyethoxy, ethoxybutoxy, benzyloxyethoxy, or enzyloxypropoxy);

hydroxyalkoxy (e.g., hydroxyethoxy, hydroxypropoxy, or hydroxybutoxy);

arylalkoxy (e.g., benzyloxy);

heterocycloalkoxy (e.g., morpholinylpropoxy, morpholinylethoxy, 3-oxo-morpholinylethoxy, pyridylethoxy, benzoxazolylmethoxy, benzoxazolylpropoxy, imidazolylethoxy, 2-oxo-oxazolidinylethoxy, 3-methyl-2-oxo-imidazolidinylethoxy, 2-hydroxy-2-pyridylethoxy);

aminoalkoxy (e.g., aminoethoxy) or aminocarbonyloxy-alkoxy (e.g., aminocarbonyloxyethoxy), especially where the amino moiety is unsubstituted or mono- or disubstituted by alkyl (e.g., methyl) or aryl (e.g., tolyl);

heterocyclocarbonylalkoxy (e.g., morpholinylcarbonylethoxy, morpholinylcarbonyl-methoxy or piperidinylcarbonylmethoxy);

heterocyclooxyalkoxy (e.g., pyridyloxyethoxy);

alkoxycarbonylalkoxy (e.g., ethoxycarbonylmethoxy); or carboxyalkoxy (e.g., carboxymethoxy); or (vi) amino ($NH_2$).

X is preferably chloro, bromo or iodo.

Particularly preferred substrates of the formula I and products of the formula II are those having the following formulae I, pref and II, pref, respectively, where the II, pref products have the (1S,2R) stereoconfiguration:

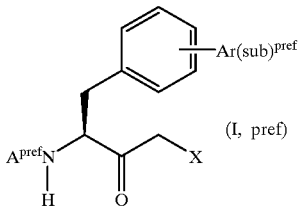

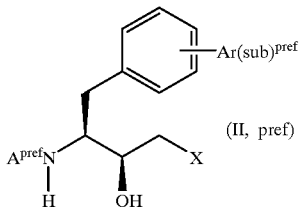

where $A^{pref}$ is acetyl, benzoyl, t-butoxycarbonyl (BOC), carbobenzoxy (Cbz), trifluoroacetyl, or fluoren-9-ylmethoxycarbonyl (FMOC);

$Ar(sub)^{pref}$ is hydrogen, hydroxy, alkyl, alkoxy (especially, substituted alkoxy such as phenylmethyloxy) or $NH_2$; and XC is Cl, Br, or I, especially Cl.

Enzymes and Microorganisms

The enzyme or microorganism employed in a method of the present invention may be any oxidoreductase enzyme, or microorganism supplying an oxidoreductase enzyme, capable of catalyzing the enzymatic reduction, preferably the stereoselective enzymatic reduction, described herein. The enyzmatic or microbial materials may be employed in the free state or immobilized on a support such as by physical adsorption or entrapment.

With respect to the use of microorganisms, the methods of the present invention may be carried out using any suitable microbial materials supplying one or more oxidoreductase enzymes capable of catalyzing the enzymatic reduction, preferably the stereoselective enzymatic reduction, described herein. For example, the cells may be used in the form of intact wet cells or dried cells such as lyophilized, spray-dried or heat-dried cells, or in the form of treated cell material such as ruptured cells or cell extracts.

Microorganisms for use in the present reduction process may include, for example, those from bacteria, yeast, and fungi genera. Exemplary genera of microorganisms include: Achromobacter, Acinetobacter, Aureobasidium, Actinomyces, Alkaligenes, Arthrobacter, Azotobacter, Bacillus, Escherichia, Brevibacterium, Corynebacterium, Flavobacterium, Methylomonas, Mycobacterium, Nocardia, Nocardioides, Pseudomonas, Rhodococcus, Streptomyces, Xanthomonas, Aspergillus, Candida, Fusarium, Geotrichum, Hansenula, Kloeckera, Penicillium, Pichia, Pullularia, Caldariomyces, Gliocladium, Schizophyllum, Mortierella, Rhizopus, Rhodotorula, Saccharomiyces, Trichoderma, Cunninghamella, Torulopsis, and Rhodopseudomonas. Preferred microorganisms include those from the following species: *Mortierella ramanniana, Streptomyces nodosus, Caldariomyces fumago, Pseudomonas cepacia, Bacillus subtilis, Bacillus cereus, Gliocladium virens, Schizophyllum commune, Aureobasidium pullulans, Arthrobacter simplex, Nocardioides albus, Nocardia globerula, Nocardia restricta, Nocardia salmonicolor, Rhodococcus fascians, Rhodococcus rhodochrous, Mycobacteriam vacca, Nocardia meditteranei, Nocardia autotrophica, Rhodococcus equi, Pullularia pullulans, Escherichia coli, Candida boidinii, Geotrichum candidum, Saccharomyces cerevisiae, Mortierella alpina, Pichia pinus, Pichia methanolica, Hansenula polymorpha, Cunninghamella echinalate, Torulopsis polysporium,* and *Acinetobacter calcoaceticus.* Most preferred microorganisms include those from the species: *Streptomyces nodosus, Candida boidinii, Caldariomyces fumago, Pullularia pullulens, Aureobasidium pullulans* and *Mortierella ramanniana,* particularly those strains employed in the Examples herein.

The use of genetically engineered microorganisms is also contemplated. The host cell may be any cell, e.g. Escherichia coli, modified to contain a gene or genes for expressing one or more enzymes capable of catalysis as described herein.

The term "ATCC" as used herein refers to the accession number of the American Type Culture Collection, 12301 Parklawn Drive, Rockville, Md. 20852, the depository for the organism referred to.

With respect to the use of enzymes, the methods of the present invention may be carried out using any suitable enzymes, regardless of origin or purity, capable of catalyzing the enzymatic reduction, preferably the stereoselective enzymatic reduction, described herein. "Oxidoreductases", also referred to as "dehydrogenases", are enzymes which catalyze an oxidation and/or reduction reaction. The enzyme employed is preferably an oxidoreductase enzyme isolated from a microorganism, such as by homogenizing cell suspensions, followed by disintegration, centrifugation, DEAE-cellulose chromatography, ammonium sulfate fractionation, chromatography using gel filtration media such as Sephacryl (cross-linked co-polymer of allyl dextran and N,N'-methylene bisacrylamide) chromatography, and ion exchange chromatography such as Mono-Q (anion exchanger which binds negatively charged biomolecules through quaternary amine groups) chromatography. The term "isolated", as used herein with respect to enzymes obtained from microorganisms, denotes at least partial, and preferably complete, separation of the remainder of the microbial materials from one or more oxidoreductase enzymes contained in or produced by the microorganism. Exemplary such enzymes include L-2-hydroxyisocaproate dehydrogenase, lactic acid dehydrogenase, yeast enzyme concentrate (Sigma), β-hydroxybutyrate dehydrogenase, glucose dehydrogenase, alcohol dehydrogenase, glycerol dehydrogenase, formate dehydrogenase, pyruvate dehydrogenase, hydroxy steroid dehydrogenase, and, most preferably, enzymes isolated from the microorganisms described above.

The compound of the formula I or salt thereof is preferably treated with *Streptomyces nodosus, Candida bodinii, Caldariomyces fumago, Pullularia pullulans, Mortierella ramanniana, Aureobasidium pullulans,* or an oxidoreductase isolated from any of these. *Streptomyces nodosus* and *Mortierella ramanniana* are the most preferred species. Preferred strains are recited in the Examples herein, particularly in Table 1 of Example 1.

When employing microorganisms, the enzymatic reduction method of the present invention may be carried out subsequent to the fermentation of the microorganism employed (two-stage fermentation and reduction), or concurrently therewith, that is, in the latter case, by in situ fermentation and reduction (single-stage fermentation and reduction).

In the single-stage process, the microorganisms may be grown in an appropriate medium (especially, containing carbon and nitrogen sources) until sufficient growth of the microorganisms is attained. A compound of the formula I or salt thereof may then be added to the microbial cultures and the enzymatic reduction continued, preferably until complete or nearly complete conversion is obtained.

In the two-stage process, the microorganisms may, in the first stage, be grown in an appropriate medium (especially, containing carbon and nitrogen sources) for fermentation until exhibiting the desired enzymatic (i.e., oxidoreductase) activity. Subsequently, the cells may be harvested, for example, by centrifugation, and microbial cell suspensions prepared, for example, by suspending harvested cells in an appropriate buffered solution. Buffers such as tris-HCl, phosphates, sodium acetate and the like may be used. Water may also be used to prepare suspensions of microbial cells. In the second stage, a compound of the formula I or salt thereof may be mixed with the microbial cell suspensions, and the enzymatic reduction of compound I or salt thereof catalyzed by the microbial cell suspensions. The reduction is continued, preferably until complete or nearly complete conversion is obtained.

Growth of the microorganisms may be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and trace elements. Inducers may also be added. The term "inducer", as used herein, denotes any compound containing keto group (s) initiating or enhancing formation of the desired enzymatic (i.e., oxidoreductase) activity within the microbial cell. Compounds of the formula I or salts thereof may be added as inducers during growth of the microorganisms.

Carbon sources may include sugars such as maltose, lactose, glucose, fructose, glycerol, sorbitol, sucrose, starch, mannitol, propylene glycol, and the like; organic acids such as sodium acetate, sodium citrate, and the like; amino acids such as sodium glutamate and the like; and alcohols such as ethanol, propanol and the like.

Nitrogen sources may include N-Z amine A, corn steep liquor, soy bean meal, beef extracts, yeast extracts, molasses, baker's yeast, tryptone, nutrisoy, peptone, yeastamin, sodium nitrate, ammonium sulfate and the like.

Trace elements may include phosphates and magnesium, manganese, calcium, cobalt, nickel, iron, sodium and potassium salts.

It is within the scope of this invention that appropriate media may include more than one carbon or nitrogen source or other nutrients and may include a mixture of several.

Preferred media include aqueous media containing the following (in weight %):

| | |
|---|---|
| Medium 1 | |
| Malt Extract | 1% |
| Yeast Extract | 1% |
| Peptone | 1% |
| Glucose | 2% |
| | pH 7.0 |
| Medium 2 | |
| Peptone | 0.3% |
| Glucose | 4% |
| Malt Extract | 1% |
| Yeast Extract | 1% |
| | pH 7.0 |
| Medium 3 | |
| Peptone | 0.3% |
| Fructose | 2% |
| Malt Extract | 1% |
| Yeast Extract | 1% |
| | pH 7.0 |
| Medium 4 | |
| Sodium Succinate | 2% |
| Malt Extract | 1% |
| Yeast Extract | 1% |
| Peptone | 0.3% |
| | pH 7.0 |

The pH of the medium is preferably adjusted to about 6 to 8, most preferably to 6.5, before sterilization. The medium is then preferably sterilized, e.g. at a temperature of 121° C. for 30 minutes, and then adjusted to a pH of about 6.5 to 7.5, most preferably 7.0, after sterilization.

The pH of the medium is preferably maintained between 4.0 and 9.0, most preferably between 6.0 and 8.0, during the growth of microorganisms and during the reduction process.

The temperature of the reaction mixture is a measure of the heat energy available for the reduction process, and should be maintained to ensure that there is sufficient energy available for the process. A suitable temperature range is from about 15° C. to about 60° C., preferably from about 25° C. to about 40° C.

The agitation and aeration of the reaction mixture affects the amount of oxygen available during the reduction process, which may be conducted, for example, in shake-flask cultures or fermentor tanks during growth of microorganisms in a single-stage or two-stage process. The agitation range from 50 to 1000 RPM is preferable, with 50 to 500 RPM being most preferred. Aeration of about 0.1 to 10 volumes of air per volume of media per minute (i.e., 0.1 to 10 v/vt) is preferred, with aeration of about 5 volumes of air per volume of media per minute (i.e., 5 v/vt) being most preferred.

Complete conversion of the compound of the formula I or salt thereof may take, for example, 5 from about 4 to 48 hours, such as 4 to 24 hours, measured from the time of initially treating said compound with a microorganism or enzyme as described herein.

The enzymatic reduction method of the present invention may be carried out using a co-factor such as nicotinamide adenine dinucleotide (NADH), especially when an isolated enzyme is employed. NADH may thereafter be regenerated and reused, for example, as described in the Examples herein. A further enzyme that regenerates the NADH (i.e., reduces NAD to NADH) may be employed such as a dehydrogenase, e.g., glucose dehydrogenase or formate dehydrogenase. Suitable hydrogen donors include molecular hydrogen, glucose, a formate (e.g. an alkali metal or ammonium formate), a hypophosphite or an electrochemical reduction in the presence of a viologen, for example methyl viologen. It is also possible to regenerate NADH without further enzymes using, for example, ethanol or formate.

It is preferred to employ an aqueous liquid as the reaction medium, although an organic liquid, or a miscible or immiscible (biphasic) organic/aqueous liquid mixture may also be employed.

It is preferred to employ 0.2 to 5 weight % of the compound of the formula I or salt thereof as starting material based on the combined weight of the compound I or salt and the reaction medium. The amount of enzyme or microorganism employed relative to the starting material is selected to allow catalysis of the enzymatic reduction of the present invention.

It is preferred to employ reaction parameters, particularly enzymes and microorganisms, which provide a stereoselective reduction. A stereoselective reduction is advantageous in that an efficient conversion of a substrate to a desired stereoisomer may be achieved, and in that the procedures which may be employed in the subsequent separation of the desired stereoisomer of the formula II or salt thereof from the remaining components of the reaction medium may be minimized. It is particularly preferred to employ parameters which provide a reaction yield greater than about 80%, most preferably greater than about 90%, and an optical purity greater than about 95%, most preferably greater than about 99%, of a desired enantiomer of the formula II. To obtain stereoselective reduction of the substrate compound of the formula I or salt thereof, it is desirable to employ the enzymes and microorganisms indicated above as preferred.

Separation

The products of the methods of the present invention may be recovered by any suitable methods for isolation and/or purification, for example, by methods such as extraction, distillation, crystallization, and column chromatography.

Preferred Utility

The halohydrins produced by the methods of the present invention may be employed as intermediates (especially, as chiral intermediates) in the preparation of renin inhibitors or of antiviral agents, particularly retroviral protease inhibitors (especially those described in European Patent Application 580,402, incorporated herein by reference in its entirety, such as [1S-[1R*,2S*(2S*,3R*)]]-[3-[[3-[[(1,1-dimethylethoxy)carbonyl]amino]-2-hydroxy-4-(4-[2(4-morpholinyl-2-oxo-ethoxy]phenyl]butyl]amino]-2-hydroxy-1-(phenylmethyl)propyl]carbamic acid, 1,1-dimethylethyl ester).

Preferably, the halohydrins of the formula II or salts thereof are converted to an epoxide of the following formula III or salt thereof:

(III)

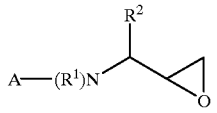

especially, an epoxide of the following formula IIIa or salt thereof:

(IIIa)

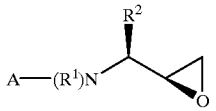

by contacting the halohydrin starting material (especially, of the formula IIa or salt thereof) with a base such as an alkali metal hydroxide (e.g., KOH) in a solvent such as ethanol. The group $R^2$ of the epoxide may optionally be converted to another group $R^2$ prior to further use. For example, where $R^2$ contains a protected hydroxyl group, the latter may be deprotected and then coupled to provide a group $R^2$ containing an alkoxy group.

It is particularly preferred to prepare HIV protease inhibitors as described in European Patent Application 580,402 employing the methods of the present invention. Preferred such inhibitors are those having the following formula IV:

(IV)

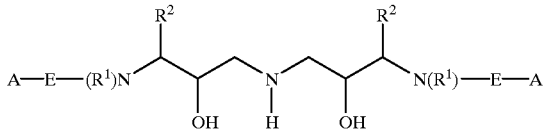

or salts thereof, particularly where the formula IV has the following stereoconfiguration IVa:

(IVa)

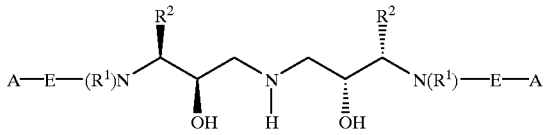

In the formulae IV and IVa, $R^1$ and $R^2$ are as defined above and each may be independently selected where it appears on opposite sides of the molecule. E is a single bond or a peptide chain containing 1 to 4 amino acids, the N-terminus of which is bonded to A, and may be independently selected where it appears on each side of the molecule.

E is preferably a single bond or a peptide chain containing 1 or 2 amino acids. Preferred amino acids are those wherein, in the formula:

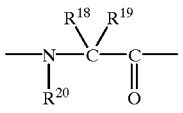

$R^{18}$ is hydrogen or unsubstituted lower alkyl (e.g., methyl);

$R^{19}$ is hydrogen, aryl (e.g., phenyl), or, most preferably, lower alkyl which is unsubstituted (e.g., methyl, isopropyl, or tert-butyl) or which is substituted, particularly by one or more of hydroxy (or protected hydroxy), amino, aminocarbonyl, fluoro (e.g., to form trifluoromethyl), phenyl, or hydroxyphenyl; or $R^{18}$ and $R^{19}$, together with the carbon atom to which they are bonded, form a cycloalkyl group (e.g., cyclopentyl); and $R^{20}$ is hydrogen or unsubstituted lower alkyl (e.g., methyl).

Compounds of the formula IV or salts thereof may be prepared from halohydrins of the formula II or salts thereof by any suitable method, such as those described in European Patent Application 580,402, incorporated herein by reference. A preferred such method is shown in the following Reaction Scheme, where A, $R^1$, $R^2$ and E are as defined above, where the superscripts "a" and "b" are used to distinguish groups on opposite sides of the compounds of the formulae IV and VI, and which begins with the epoxide III obtained from a halohydrin II as described above.

Reaction Scheme

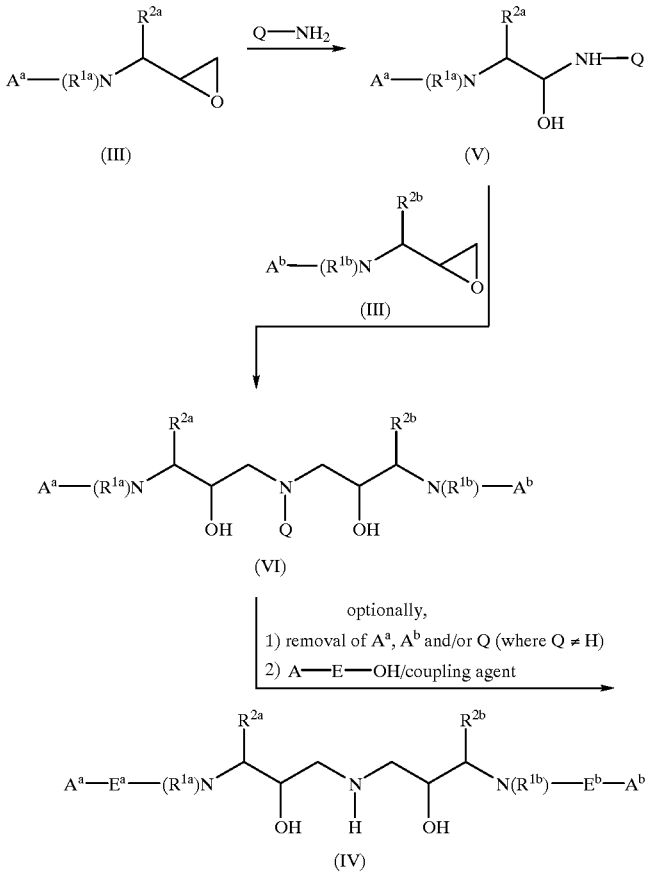

In the above Reaction Scheme, a compound of the formula III or salt thereof is contacted with a compound $Q—NH_2$, preferably in the presence of a metal halide such as LiCl, LiBr, or $LiClO_4$, to yield a compound of the formula V or salt thereof. Q is hydrogen or alkyl, and is preferably a group rendering the nitrogen atom to which it is bonded basic. Exemplary Q groups are hydrogen, unsubstituted lower alkyl, alkenyl-lower alkyl and aryl-lower alkyl, especially benzyl.

The compound of the formula V or salt thereof is then contacted with a compound of the formula III or salt thereof, which may be the same as or different from the compound of the formula III or salt thereof used in the previous step, to form a compound of the formula VI or salt thereof.

To obtain a compound of the formula IV or salt thereof: (a) where Q is other than hydrogen, Q may be removed by any suitable method, such as by hydrogenation with hydrogen gas and $Pd(OH)_2$ catalyst when Q is benzyl; and (b) where a different group A is desired, or E is other than a single bond, the groups $A^a$ and/or $A^b$ of the compound of the formula VI or salt thereof may be removed by any suitable method to yield a terminal group $H(R^1)N$—, and the desired group A and/or group E then added. For example, a compound of the formula A—E—OH may be added in the presence of a coupling agent to form an amide group with the terminal group $H(R^1)N$— of the compound of the formula VI or salt thereof.

The HIV protease inhibitors prepared as described herein are particularly useful in the prevention and/or treatment of infection by HIV viruses (HIV-1, HIV-2, and mutants thereof), including the treatment of consequent pathological conditions such as AIDS.

The present invention is further described by the following examples which are illustrative of preferred embodiments only, and are in no way intended to limit the scope of the claims appended hereto.

EXAMPLE 1

USE OF VARIOUS MICROBIAL STRAINS TO CONDUCT REDUCTION PROCESS: WHOLE CELLS

This Example illustrates the present reduction process, employing a variety of microbial strains in the form of whole cells.

The substrate used was the enantiomer (1S)-[3-chloro-2-oxo-1-(phenylmethyl)propyl]carbamic acid, 1,1-dimethylethyl ester, hereinafter referred to as compound A, having the following structure:

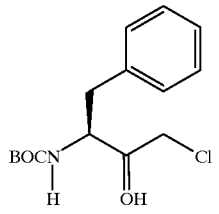

where "BOC" denotes tert-butoxycarbonyl. The product sought was the enantiomer (1S,2R)-[3chloro-2-hydroxy-1-(phenylmethyl)propyl]carbamic acid, 1,1-dimethylethyl ester, hereinafter referred to as compound B, having the following structure:

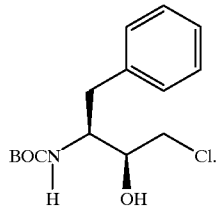

The microorganisms were maintained in a vial in liquid nitrogen. For routine development of inoculum, one vial (1 mL) was inoculated into 100 mL of Medium 1 (the composition of which is described above) in a 500 mL flask and incubated at 28° C. and 280 RPM on a shaker for 48 hours. After growth of the microorganisms, 10 mL of culture was inoculated into a 500 mL flask containing 100 mL of Medium 1 and incubated at 28° C. and 250 RPM on a shaker for 24 hours.

The cells were then harvested by centrifugation and suspended in 100 mM potassium phosphate buffer, pH 6.8. 10 mL of 20% w/v cell suspensions were prepared. The cell suspensions were supplemented with 10 mg of substrate (compound A) and 750 mg of glucose and the biotransformations (reductions) were conducted at 28° C., 150 RPM for 48 hours. One volume of sample was taken and extracted with five volumes of 60:40 t-butylmethyl ether:toluene, and the separated organic phase was filtered through a 0.2 μm filter and collected.

Two mL of the organic layer was taken and resuspended in 1 mL ethanol prior to the following HPLC analysis.

HPLC

A 20 μl sample obtained as above was injected onto a YMC-PACK ODS-A column (100×4.5 mm I.D., 5 micron). Samples were eluted at 1 ml/min. in a biphasic system consisting of 10% methanol (solvent A) and 90% methanol (solvent B) and monitored at 220 nm, 254 nm, and 280 nm. Elution was conducted according to the following time table:

| Time (minutes) | Solvent A | Solvent B |
|---|---|---|
| 0 | 100% | 0 |
| 25 | 25% | 75% |
| 25.2 | 100% | 0% |
| 30 | 100% | 0% |

Compounds A and B eluted at 24.0 and 23.5 minutes, respectively. Where the undesired stereoisomer, hereinafter referred to as compound C, having the following structure:

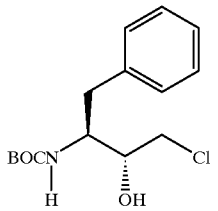

was formed, that compound eluted at 24.5 minutes.

The results obtained by using various microorganisms grown on Medium 1 and following the above procedures are shown in the following Table 1.

TABLE 1

| Microorganism | ATCC No. | Diastereomeric Purity | Yield (%) |
|---|---|---|---|
| *Escherichia coli* | 8739 | 100% | 8% |
| *Streptomyces nodosus* | 14899 | 100% | 36% |
| *Pullularia pullulans* | 16624 | 81% | 47% |
| *Pichia pinus* | 28780 | 78% | 37% |
| *Caldariomyces fumago* | 11925 | Run 1: 93% | 33% |
| | | Run 2: 91% | 51% |
| *Candida boidinii* | 26175 | 100% | 39% |
| *Pseudomonas cepacia* | 29351 | 85% | 11% |
| *Nocardioides albus* | 55424 | 92% | 5% |
| *Bacillus subtilis* | 9799 | 100% | 1% |
| *Bacillus cereus* | 27348 | 100% | 1% |
| *Gliocladium virens* | 44327 | 65% | 16% |
| *Schizophyllum commune* | 38548 | 100% | 1% |
| *Aureobasidim pullulans* | 42457 | 87% | 44% |
| *Pseudomonas sp.* | 21808 | 100% | 4% |
| *Mortierella ramanniana* | 24786 | 91% | 54% |
| *Pichia methanolica* | 56510 | 68% | 35% |

In Table 1, "Diastereomeric Purity" was calculated as: {([B])÷([B]+[C])}×100, where [B] was the amount of compound B formed, and [C] was the amount of compound C formed. The "Yield" (wgt %) in Table 1 was calculated as: {([B]+[C])÷([A])}×100, where [A] was the amount of compound A employed as substrate.

To determine whether epimerization occurred at the carbon atom bearing the benzyl group, that is, whether any compound D having the following structure was formed:

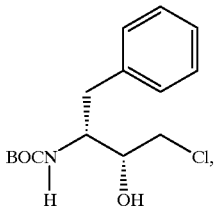

the optical purity was determined using the following HPLC method. All samples obtained by the above method were evaporated to dryness, redissolved in mobile phase and filtered through a 0.22 μm nylon-66 filter.

HPLC: Hewlett Packard (Hewlett-Packard, Kennett Square, Pa.) or comparable equipped with a photo diode array detector at 210 nm

| | |
|---|---|
| Mobile Phase: | 97.5% hexane<br>1.5% ethyl alcohol<br>1.0% cyclohexanol |
| HPLC Column: | 25 cm × 4.6 mm (i.d.) 5 μm; Chiralpak AD; Diacel Chemical Industries, Ltd. |
| Flow Rate: | 0.8 ml/min |
| Column Temperature: | 28° C. |
| Retention Time: | 14.0 minutes for compound A<br>15.5 minutes for compound B<br>21.5 minutes for compound D |

The optical purity of compound B, calculated as {([B])÷([B]+[D])}×100, was 100% (that is, compound D was not produced) for all microbial cultures evaluated.

EXAMPLE 2

USE OF WHOLE CELLS: TWO STAGE PROCESS

The substrate for this process, compound A, and the desired product, compound B, were as described in Example 1.

Cells of *Mortierella ramanniana* ATCC 24786 were grown in 100 mL of Medium 1 (described above) combined in a 500 mL flask. Growth was carried out at 25° C. for 48 hours at 280 RPM. 100 mL of cultures were inoculated into 15 L of Medium 2 (described above) combined in a fermentor. Growth in the fermentor was carried out at 25° C., 15 LPM (liters per minute) aeration and 500 RPM agitation for 30 hours. Cells were harvested from the fermentor and used for the enzymatic conversion (biotransformation) of compound A to compound B.

Homogenous cell suspensions were prepared by suspending the cells (300 grams) in 3 liters of 100 mM potassium phosphate buffer, pH 6.8. 3 Grams of compound A and 75 grams of glucose were added to the cell suspensions and the biotransformation of compound A to compound B was carried out at 28° C., 160 RPM for 24 hours. The results which were obtained are summarized in the following Table 2. Samples were prepared, and product yield, diastereomeric and optical purity were determined, as described in Example 1.

TABLE 2

| Reaction Time (hours) | Compound B g/L | Yield (%) | Optical purity (%) | Diastereomeric purity (%) |
|---|---|---|---|---|
| 12 | 0.22 | 22 | 100 | 90 |
| 24 | 0.54 | 54 | 100 | 91 |

EXAMPLE 3

USE OF WHOLE CELLS: SINGLE-STAGE PROCESS

The substrate for this process, compound A, and the desired product, compound B, were as described in Example 1.

Cells of *Streptomyces nodosus* ATCC 14899 were grown in 100 mL of Medium 1 (described above) combined in a 500-mL flask. Growth was carried out at 25° C. for 48 hours at 280 RPM. 100 mL of cultures were inoculated into 15 L of Medium 2 (described above) combined in a fermentor. Growth in the fermentor was carried out at 25° C., 15 LPM aeration and 500 RPM agitation for 30 hours. After the 30 hour growth period, 15 grams of substrate (compound A) were added to the fermentor and the biotransformation process was started under the same fermentation conditions employed during the initial 48 hours of growth. The results which were obtained are summarized in the following Table 3. Samples were prepared, and product yield, diastereomeric and optical purity were determined, as described in Example 1.

TABLE 3

| Reaction Time (hours) | Compound B g/L | Yield (%) | Optical purity (%) | Diastereo-meric purity (%) |
|---|---|---|---|---|
| 24 | 0.56 | 56 | 100 | 100 |
| 48 | 0.67 | 67 | 100 | 100 |

Compound B was isolated from 150 ml of the fermentation reaction mixture containing 105 mg of compound B according to the following procedure:

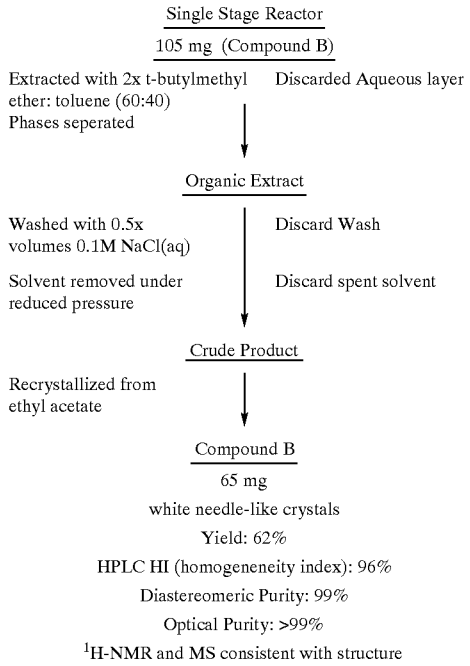

EXAMPLE 4

USE OF CELL EXTRACTS AND CO-FACTOR

The substrate for this process, compound A, and the desired product, compound B, were as described in Example 1.

Cells of *Streptomyces nodosus* ATCC 14899 and *Mortierella ramanniana* ATCC 24786 were grown on Medium 1 and Medium 2 as described in Examples 2 and 3.

Cells (150 grams) were suspended in 20 mL of 0.1M potassium phosphate buffer, pH 6.8. The homogenized cell suspensions were disintegrated at 4° C. by use of a Microfluidizer at 13,000 psi pressure. The disintegrated cell suspension was centrifuged at 12,000 RPM for 30 minutes. The clear supernatant ("cell extracts") was used for the biotransformation of compound A to compound B.

10 mL of each cell extract was supplemented with 10 mgs of substrate (compound A), glucose dehydrogenase (35 units), 0.7 mM $NAD^+$ (nicotinamide adenine dinucleotide), and 200 mgs of glucose. The reaction was carried out in a pH stat at pH 6.0, 150 RPM agitation, and 30° C. Periodically, samples were taken and analyzed for the reaction yield, diastereomeric purity and optical purity of compound B as described in Example 1. The results which were obtained are shown in the following Table 4.

TABLE 4

| Organisms | Reaction Time (hours) | Compound B mg/mL | Yield (%) | Opti-cal purity (%) | Diaster-eomeric purity (%) |
|---|---|---|---|---|---|
| *M. ramanniana* ATCC 24786 | 20 | 0.52 | 52 | 100 | 94 |
| *S. nodosus* ATCC 14899 | 20 | 0.65 | 65 | 100 | 100 |

In the above Example, the NADH cofactor used for the biotransformation of compound A to compound B was regenerated using glucose dehydrogenase, $NAD^+$, and glucose as shown below.

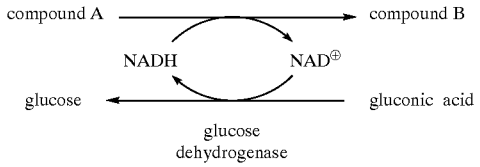

What is claimed is:

1. A method for the enzymatic reduction of a compound of the formula I or a salt thereof:

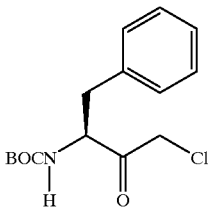

where BOC is tert-butoxycarbonyl, to form a compound of the formular II or a salt thereof:

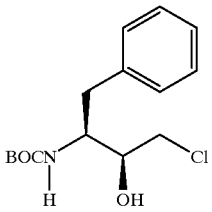

comprising the steps of contacting said compound of the formula I or salt thereof with an oxidoreductase enzyme-supplying microorganism or oxidoreductase enzyme-containing material obtained from said microorganism, capable of catalyzing the reduction of said compound of the formula I or salt thereof to form said compound of the formula II or salt thereof, and effecting said reduction, where said microorgaism is selected from the group consisting of *Escherichia coli,* ATCC 8739; *Streptomyces nodosus,* ATCC 14899; *Pullularia pullulans,* ATCC 16624; *Pichia pinus,* ATCC 28780; *Caldariomyces fumago,* ATCC 11925; *Candida*

*boidinii,* ATCC 26175: *Pseudomonas cepacia,* ATCC 29351; *Nocardioides albus,* ATCC 55424; *Bacillus subtilis*, ATCC 9799; *Bacillus cereus,* ATCC 27348; *Gliocladium virens,* ATCC 44327; *Schizophyllum commune,* ATCC 38548; *Aureobasidium pullulans,* ATCC 42457; *Pseudomonas sp.,* ATCC 21808; *Mortierella ramanniana,* ATCC 24786, and *Pichia methanolic,* ATCC 56510.

* * * * *